United States Patent
Ben-Haim et al.

(10) Patent No.: US 6,304,777 B1
(45) Date of Patent: Oct. 16, 2001

(54) INDUCTION OF CARDIOPLEGIA APPLIED ELECTRICAL SIGNALS

(75) Inventors: Shlomo Ben-Haim; Nissim Darvish, both of Haifa; Yuval Mika, S. Zichron Yaakov; Benny Rousso, Bat Yam; Bella Felzen, Haifa, all of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/320,091

(22) Filed: May 26, 1999

(51) Int. Cl.[7] ............................... A61N 1/32; A61N 1/36
(52) U.S. Cl. ........................................ 607/2; 607/1; 607/9
(58) Field of Search ...................... 607/1, 2, 4, 9

(56) References Cited

U.S. PATENT DOCUMENTS

| | | |
|---|---|---|
| 3,572,345 | 3/1971 | Auphan . |
| 3,587,567 | 6/1971 | Schiff . |
| 5,468,254 | 11/1995 | Hahn . |
| 5,584,803 * | 12/1996 | Stevens et al. ........................ 604/4 |
| 5,651,378 | 7/1997 | Matheny ............................ 607/10 |
| 5,674,259 | 10/1997 | Gray . |
| 5,814,079 | 9/1998 | Kieval . |
| 5,913,876 * | 6/1999 | Taylor et al. ........................ 607/2 |

FOREIGN PATENT DOCUMENTS

| | | |
|---|---|---|
| WO 97/25098 | 7/1997 | (WO) . |
| WO 98/10830 | 3/1998 | (WO) ........................... A61N/1/362 |
| WO 98/10832 | 3/1998 | (WO) . |

OTHER PUBLICATIONS

"Vagus Nerve Stimulation as a Method to Temporarily Slow or Arrest the Heart", by Matheny and Shaar, Annals of Thoracic Surgery, 63(6) Supplement (Jun. 1997), pp. S–28–29.

"Prevention of Action Potentials During Extracellular Electrical Stimulation of Long Duration", Xiaohong Zhou, et al., Journal of Cardiovascular Electrophysiology, vol. 8, No. 7, Jul. 1997, pp. 779–789.

C. D. Swerdlow et al., "Cardiovascular collapse caused by electrocardiographically silent 60–Hz intracardiac leakage current: Implications for electrical safety"., *Circulation*. 99(19), pp. 2559–2564: May 18, 1999.

R.A. Malkin and B.K. Hoffmeister, "AC Leakage Currents Cause Complete Hemodynamic Collapse below the Ventricular Fibrillation Threshold", Computers in Cardiology Annual Conference, Hanover, Germany, Sep. 1999.

Hayashi et al., "Right Vagal Nerve Stimulation During Minimally Invasive Direct Coronary Artery Bypass Grafting in Dogs. A Preliminary Study", *Journal of Cardiovascular Surgery* (Torino), 39:4, Aug.1998, pp. 469–471.

* cited by examiner

Primary Examiner—Carl Layno
(74) Attorney, Agent, or Firm—Cowen, Liebowitz & Latman, P.C.; William H. Dippert (57) ABSTRACT

A method and apparatus for controlling activity of a heart of a living person during a medical procedure. Electrical signals are applied to the heart so as to induce a spontaneously-reversible cardioplegia thereof. The signals are preferably such that terminating application of the signals does not induce fibrillation. Most preferably, the signals have an amplitude that is below a level that would induce fibrillation upon termination thereof.

22 Claims, 5 Drawing Sheets

INDUCTION OF CARDIOPLEGIA APPLIED ELECTRICAL SIGNALS

FIELD OF THE INVENTION

The present invention relates generally to invasive devices and methods for treatment of the heart, and specifically to devices and methods for controlling the heart muscle during surgery.

BACKGROUND OF THE INVENTION

Induction of cardioplegia is known in the art as a means for the temporary and elective stopping of cardiac activity by injection of chemicals, selective hypothermia, mechanical stabilization, or electrical stimuli. It is most commonly used in preparation for cardiac surgery.

PCT patent application PCT/IL97/00012, published as WO 97/25098, to Ben-Haim et al., which is incorporated herein by reference, describes methods for modifying the force of contraction of at least a portion of a heart chamber by applying a non-excitatory electrical signal to the heart at a delay after electrical activation of the portion. The signal may be applied in combination with a pacemaker or defibrillator, which also applies an excitatory signal (i.e., pacing or defibrillation pulses) to the heart muscle.

PCT patent application PCT/IL97/00236, which is also incorporated herein by reference, describes a pacemaker that modifies cardiac output. This pacemaker applies both excitatory (pacing) and non-excitatory electrical signals to the heart. By applying non-excitatory signals of suitable strength, appropriately timed with respect to the heart's electrical activation, the contraction of selected segments of the heart muscle can be increased or decreased, thus increasing or decreasing the stroke volume of the heart. The PCT application suggests that pacing electrodes may be placed in two, three or all four chambers of the heart, in accordance with methods of multi-chamber pacing known in the art.

U.S. Pat. No. 5,651,378 to Matheny et al., and an article entitled, "Vagus Nerve Stimulation as a Method to Temporarily Slow or Arrest the Heart," by Matheny and Shaar, *Annals of Thoracic Surqery*, 63 (6) Supplement (June 1997), pp. S28–29, which are both incorporated herein by reference, describe a method to stimulate the vagus nerve in order to slow or stop a patient's heart during coronary artery bypass grafting surgery. While these methods describe electrically-stimulating the vagus nerve, they are, overall, substantially similar to chemical means of inducing cardioplegia, and are therefore characterized by a generally slow time constant following application and removal of the vagal nerve stimulation.

SUMMARY OF THE INVENTION

It is an object of some aspects of the present invention to provide improved methods and apparatus for regulating motion of the heart.

It is a further object of some aspects of the present invention to provide improved methods and apparatus for reducing motion of the heart during open-heart surgery.

In preferred embodiments of the present invention, an electrical cardiac stimulator for inducing cardioplegia comprises one or more electrodes, placed at multiple sites in or on the heart of a patient, and an electrical control unit. The control unit administers a signal comprising a sequence of pulses to at least one of the electrodes in order to reduce or substantially stop motion of the heart for the duration of signal application. Termination of signal application allows the heart to resume normal beating. Preferably, the level of paralysis of the heart produced during the pulse application is sufficiently complete to allow a surgeon to perform open-heart surgery or minimally-invasive surgery on the substantially non-moving heart. Further preferably, the high rate of response of the heart to application and termination of the signal enables the surgeon to perform the surgery without using cardiopulmonary bypass. Still further preferably, termination of signal application is not characterized by fibrillation of the heart. Fibrillation, in the context of the present patent application, refers to the disorganized, rapid, and agitated contraction of fibrils of a muscle, and is not generally characterized by spontaneous recovery.

Preferably, the signal comprises a sequence of rapid pacing pulses, applied through one or more of the electrodes, in order to induce a state of generally constant contraction of most or substantially all of the heart muscle. For example, a plurality of endocardial electrodes may be used to apply a signal above 5 Hz to the heart, in order to induce cardioplegia.

Typically, short periods of pulse application are separated by longer periods wherein cardioplegia is not induced. Preferably, the durations of the pulse application and non-application periods are set to maximize the surgeon's time for performing surgery, while continuing to generally assure that the patient's systemic oxygen needs are satisfied.

In some preferred embodiments of the present invention, at least some of the electrodes are placed at multiple sites on the epicardium and/or endocardium of the left and right ventricles. Alternatively or additionally, some of the electrodes are trans-venous and/or trans-arterial electrodes, and are typically inserted through a catheter into epicardial or other blood vessels in a vicinity of the heart.

Typically, each electrode coupled to the control unit conveys a particular waveform to the heart, which may differ in certain aspects from the waveforms applied to other electrodes. The particular waveform is preferably determined by the unit under the control or supervision of a human operator. Aspects of the waveforms which are set by the control unit typically include, but are not limited to, parameters such as time shifts between application of signals at different electrodes, signal shapes, amplitudes, DC offsets, pulse durations, frequencies and duty cycles.

In some preferred embodiments of the present invention, a "fencing" signal is additionally applied at one or more locations in or on the heart, in order to inhibit an action potential from developing, and/or to prevent an action potential from propagating from one region of the heart to another. Such fencing is described in PCT patent application PCT/IL97/00233 and in a U.S. patent application filed in the national phase thereof, which are incorporated herein by reference. Fencing is typically used, according to these embodiments, to block or reduce the normal transmission of signals, generally yielding thereby a reduction of the force of contraction of the heart.

In some preferred embodiments of the present invention, one or more motion sensors, e.g., accelerometers, are coupled to or disposed near the heart, and send signals to the control unit indicative of cardiac motion. The motion signals serve as feedback, to enable the control unit to adjust some or all of the above-described electrical stimuli responsive to the signals. Preferably, the motion sensors allow the control unit to calibrate the electrical stimuli which it delivers to the heart, in order to attain a desired level of stabilization of the heart.

In some preferred embodiments of the present invention, one or more sensors, e.g., local electrical activity sensors and/or a Left Ventricular Pressure (LVP) sensor, monitor the heart's behavior to detect an abnormal, potentially-dangerous condition, such as fibrillation. Algorithms and/or circuitry associated with the control unit which detect the condition preferably discontinue signal application and initiate defibrillation and/or cardioversion procedures.

Preferably, application of the electrical stimuli in accordance with the present invention stabilizes the heart within a very short period, typically about 1 second, and can maintain the stability of the heart for prolonged periods, for example, 100 seconds, in order to allow a surgeon to perform surgery on a substantially non-moving heart. The heart typically returns to normal function within about 2 seconds of removal of the electrical stimuli.

There is therefore provided, in accordance with a preferred embodiment of the present invention, a method for controlling activity of a heart of a living person during a medical procedure, including applying electrical signals to the heart so as to induce a spontaneously-reversible cardioplegia thereof.

Preferably, the signals are such that terminating application of the signals does not induce fibrillation. Most preferably, the signals have an amplitude that is below a level that would induce fibrillation upon termination thereof.

Preferably, the signals cause contraction of muscle tissue of the heart.

In a preferred embodiment, applying the signals includes applying pulses at a rate greater than 5 Hz, and most preferably at a rate greater than 10 Hz.

Preferably, applying the signals includes:

intermittently applying pulses, to substantially stop motion of the heart; and intermittently removing the pulses, to enable the heart to pump blood.

Preferably, intermittently removing the pulses includes:

sensing electrical activity of the heart to detect arrhythmia thereof; and applying electrical energy to the heart to treat the arrhythmia.

Further preferably, intermittently applying pulses includes:

sensing electrical activity of the heart to detect arrhythmia thereof; and applying electrical energy to the heart to treat the arrhythmia.

In a preferred embodiment, the method includes performing thoracic surgery on the person while the heart is in the cardioplegic state.

In another preferred embodiment, the method includes performing a diagnostic procedure on the person while the heart is in the cardioplegic state.

In still another preferred embodiment, the method includes sensing motion of the heart, wherein applying the pulses includes modifying a characteristic of at least some of the signals applied to the heart responsive to the sensed motion. Preferably, sensing the motion includes coupling at least one motion sensor to detect motion of a portion of the heart, wherein modifying the characteristic includes modifying a signal characteristic so as to reduce the motion of the portion of the heart.

In yet another preferred embodiment, the method includes applying a fencing signal to the heart to inhibit propagation of an activation wave therein while applying the electrical pulses.

Preferably, applying the electrical signals includes applying signals at a plurality of sites on the heart, wherein applying the signals includes applying a first waveform at a first one of the sites and applying a second waveform, which differs from the first waveform, at a second one of the sites.

In still another preferred embodiment, applying the electrical signals includes applying a first signal so as to precondition a response of the heart to a subsequent signal, which induces the cardioplegia.

There is also provided, in accordance with a preferred embodiment of the present invention, a method for controlling activity of a heart of a living person during a medical procedure, including:

inducing cardioplegia of the heart, such that activity of the heart is reduced to a target level within 3 seconds of initiating such induction;

maintaining the cardioplegia for at least 10 seconds; and terminating the cardioplegia, such that the heart resumes substantially normal function within 3 seconds.

There is also provided, in accordance with a preferred embodiment of the present invention, apparatus for controlling activity of a heart of a living person during a medical procedure, including:

one or more electrodes, coupled to the heart; and a control unit, which actuates the electrodes to apply electrical signals to the heart so as to induce a spontaneously reversible cardioplegia thereof.

Preferably, the electrodes include one or more local sense electrodes, coupled to the heart and to the control unit, which sense electrical activity of the heart to detect arrhythmia thereof, and convey a signal responsive to the sensing to the control unit.

Alternatively or additionally, the apparatus includes one or more motion sensors, coupled to the heart and to the control unit, which sense motion of the heart, wherein the control unit adjusts the signals applied to the heart responsive to the motion, wherein the control unit adjusts the signals so as to minimize the sensed motion.

In a preferred embodiment, the apparatus includes one or more fencing electrodes, coupled to the heart, which are actuated by the control unit to apply a fencing signal to the heart so as to inhibit propagation of an activation wave therein.

There is further provided, in accordance with a preferred embodiment of the present invention, apparatus for controlling activity of a heart of a living person during a medical procedure, which induces cardioplegia of the heart, such that activity of the heart is minimized within 3 seconds of initiating such induction, maintains the cardioplegia for at least 10 seconds, and terminates the cardioplegia, such that the heart resumes substantially normal function within 3 seconds.

There is further provided, in accordance with a preferred embodiment of the present invention, a method for performing a medical procedure on a muscle, including:

applying electrical signals to the muscle so as to reduce activity thereof, such that the activity increases spontaneously upon removal of the signals; and performing the procedure while the activity is reduced.

Preferably, the muscle includes heart muscle or, alternatively or additionally, smooth muscle or skeletal muscle.

Preferably, performing the procedure comprises performing a diagnostic procedure or, alternatively or additionally, a therapeutic procedure.

There is moreover provided, in accordance with a preferred embodiment of the present invention, apparatus for performing a medical procedure on a muscle, including:

one or more electrodes, coupled to the muscle; and a control unit, which actuates the electrodes to apply electrical signals to the muscle so as to reduce activity thereof, whereby the procedure is performed on the segment, and such that the activity increases spontaneously upon removal of the signals.

The present invention will be more fully understood from the following detailed description of the preferred embodiments thereof, taken together with the drawings, in which:

DETAILED DESCRIPTION OF PREFERRED EMBODIMENTS

Figure 1:
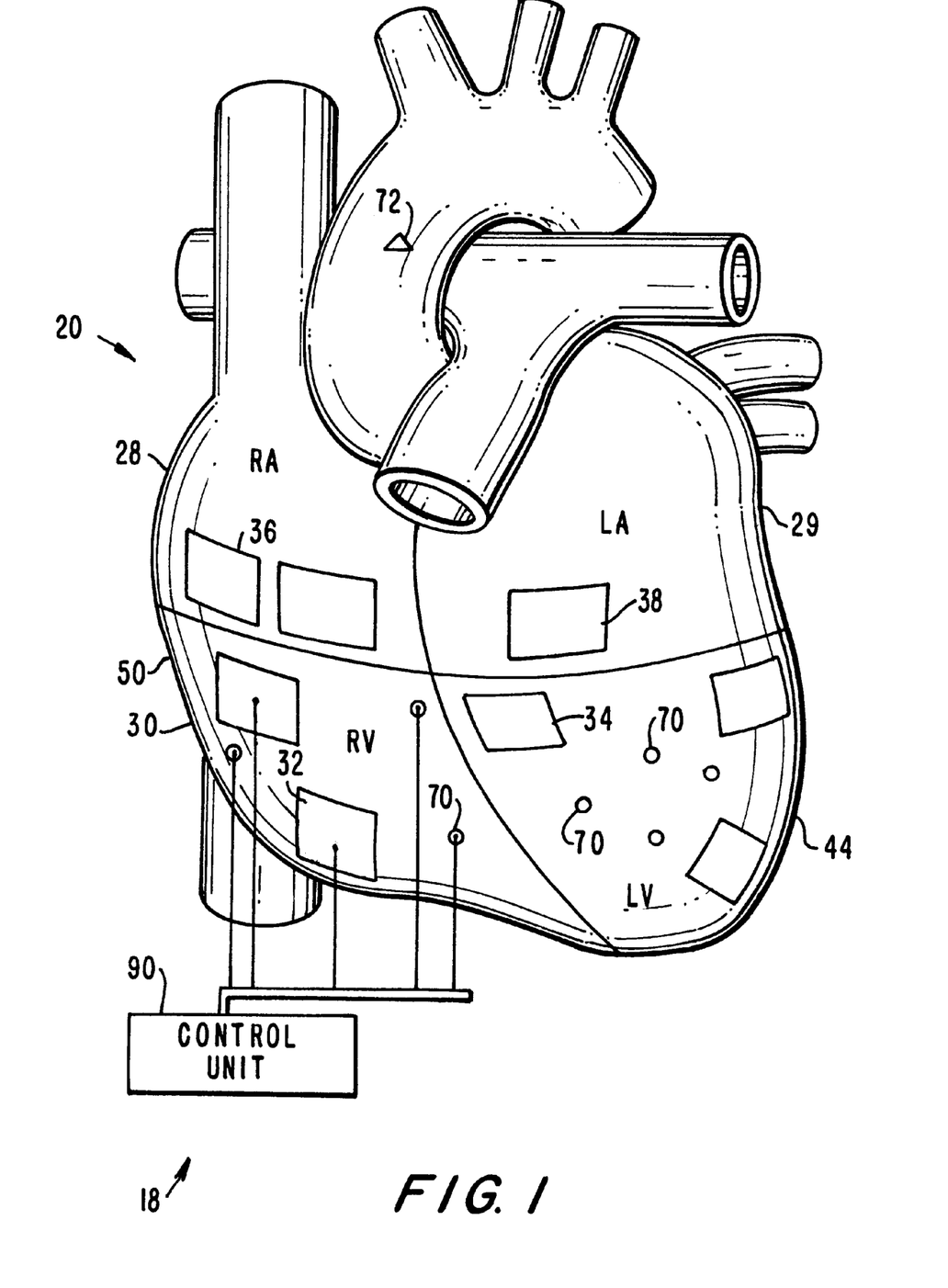
FIG. 1 a schematic illustration of the external surface of a heart, showing the placement of patch electrodes thereon, in accordance with a preferred embodiment of the present invention.

FIG. 1 is a schematic illustration of apparatus 18 for inducing cardioplegia of a patient's heart 20, in accordance with a preferred embodiment of the present invention. One or more patch electrodes 32, 34, 36, and 38, are coupled to the epicardium 50 overlying, respectively, the right and left ventricles 30 and 44 and right and left atria 28 and 29. Additionally, optional motion sensors 70 (e.g., accelerometers) and one or more optional supplemental sensors 72 (e.g., Left Ventricular Pressure (LVP), systemic blood pressure, ECG, pCO2, pO2, and flow rate sensors) are coupled to the heart or placed elsewhere on or in the patient's body. A control unit 90, preferably coupled to all of the electrodes and sensors, is used to control heart activity, and specifically to induce intermittent cardioplegia during cardiac surgery, as described further hereinbelow. For clarity, connections between control unit 90 and only some of the electrodes and sensors are shown in FIG. 1.

Preferably, control unit 90 continuously reports the measurements of the sensors to an operator of apparatus 18, who interprets the measurements to determine the patient's current cardiac and systemic status. Responsive thereto, the operator may choose to continue the cardioplegia-inducing procedure substantially unchanged, modify the procedure in order to improve some or all of the measurements, or, if a dangerous condition is detected, terminate the induction of cardioplegia and initiate defibrillation, cardioversion, or other appropriate steps.

Figure 2:
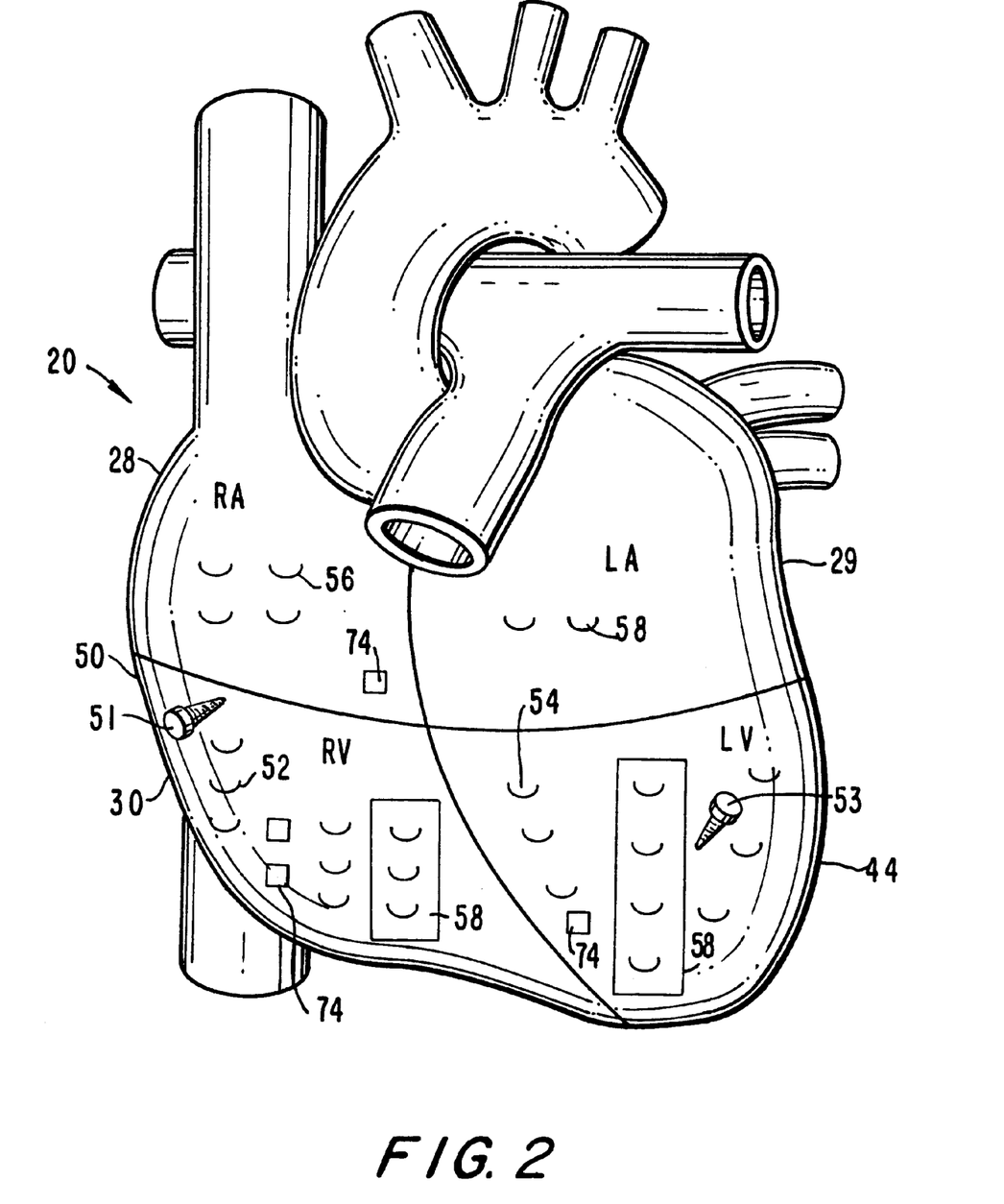
FIG. 2 is a schematic illustration of the external surface of a heart, showing the placement of needle and screw electrodes thereon, in accordance with a preferred embodiment of the present invention.

FIG. 2 is a schematic illustration showing the placement of one or more screw electrodes 51 and 53 and needle and/or wire electrodes 52, 54, and 56 onto epicardium 50, in accordance with another preferred embodiment of the present invention. Preferably, the electrodes shown in FIG. 2 are coupled to control unit 90 (not shown). Some of the needle and/or wire electrodes are optionally coupled to strips 58, which are themselves coupled to heart 20, in order to improve the coupling between the electrodes and the heart and to increase ease of use. Local sense electrodes 74, are preferably coupled to the epicardium or placed within one or more chambers of the heart, and convey electrical signals responsive to cardiac electric activity to circuitry described hereinbelow with reference to FIG. 4. Alternatively or additionally, the screw, needle, or wire electrodes may be used for local sensing, as well as stimulation.

Figure 3:
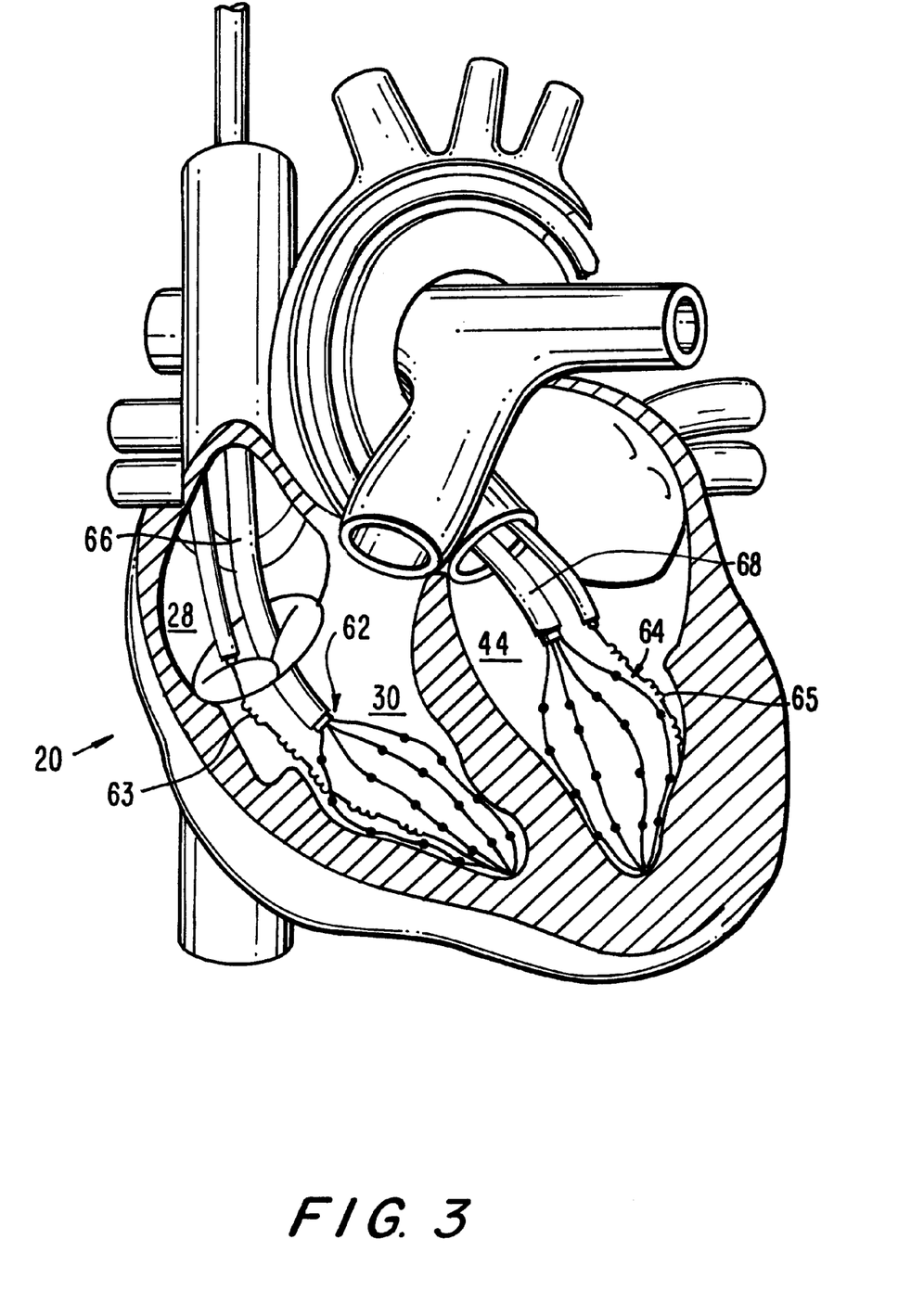
FIG. 3 is a schematic, sectional illustration of a heart, showing the placement of endocardial basket electrodes, coil electrodes, and defibrillation electrodes, in accordance with a preferred embodiment of the present invention.

FIG. 3 is a schematic, sectional illustration of heart 20, showing the placement of endocardial basket electrodes 62 and 64, and defibrillation and/or coil electrodes 63 and 65, in accordance with a preferred embodiment of the present intention. Preferably, the electrodes shown in FIG. 3 are coupled to control unit 90 (not shown). Catheters 66 and 68 preferably pass basket electrodes 62 and 64 through the vena cava and aorta, respectively, and subsequently actuate basket electrodes to open in the ventricles. Electrodes 63 and 65 are preferably positioned in their respective locations in a similar manner.

It will be understood by one skilled in the art that the types and placement of electrodes in FIGS. 1–3 are shown by way of example. Other sites in and around the heart are appropriate for electrode or sensor placement in other applications of the present invention. For example, trans-arterial and/or trans-venous electrodes (not shown) may be conveyed by catheter to a location in a vicinity of the heart, and subsequently actuated to transmit energy through the vessel wall to a region of the heart. Additionally, different numbers of electrodes or sensors (including no electrodes or sensors in some areas) and different types and combinations of the above-cited sensors and patch, coil, defibrillation, needle, wire, and basket electrodes may be used in applying the principles of the present invention. Furthermore, for some applications it is desirable to apply signals between two electrodes, while in other applications it is desirable to apply signals between an electrode and the patient's body.

Figure 4:
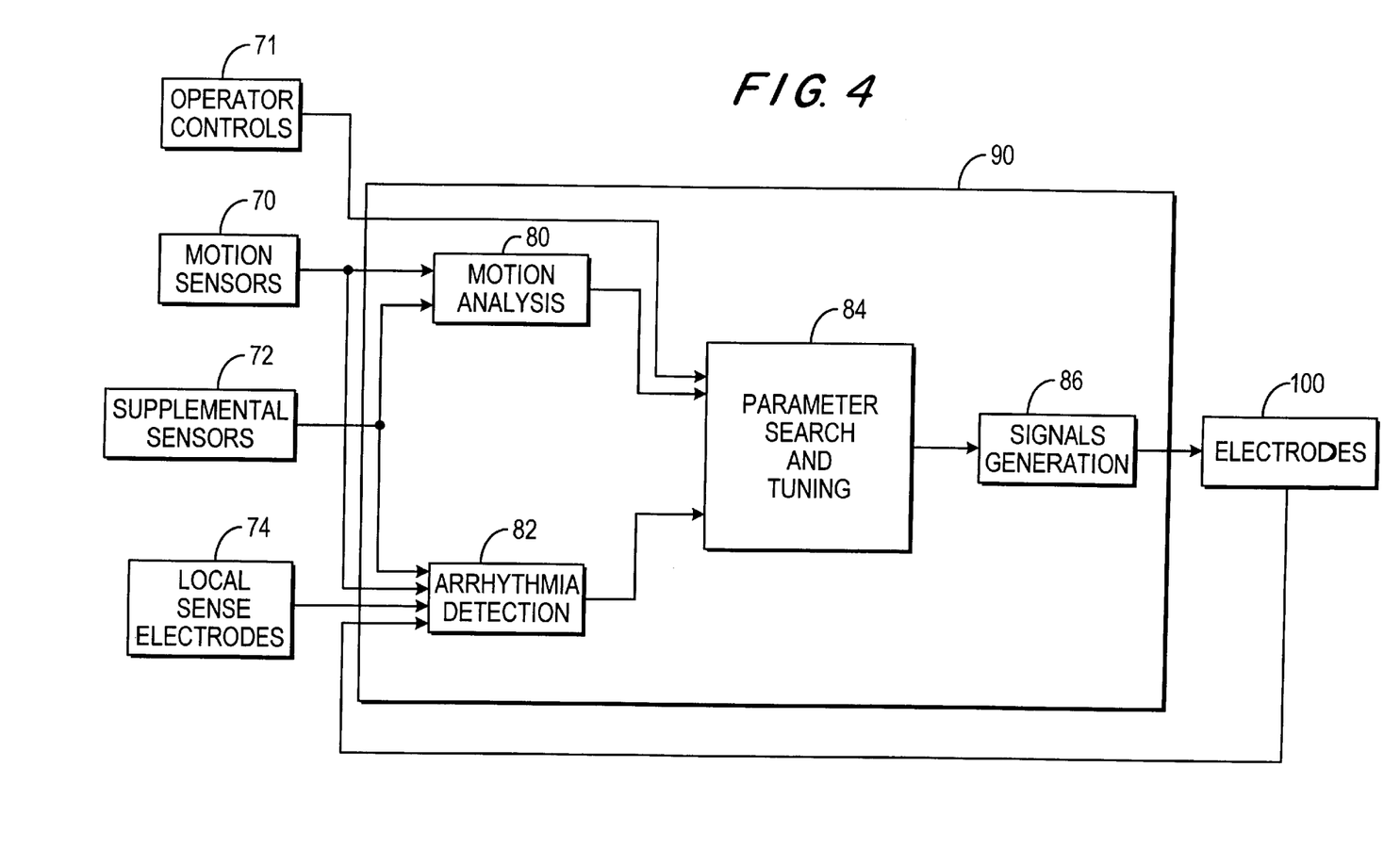
FIG. 4 is a schematic block diagram of a control unit, which generates signals to be applied to the electrodes shown in the preceding figures, in accordance with a preferred embodiment of the present invention.

FIG. 4 is a schematic block diagram of control unit 90, which conveys electrical energy to electrodes 100 coupled to heart 20 in order to induce cardioplegia, in accordance with a preferred embodiment of the present invention. Typically, electrodes 100 comprise one or more of the electrodes shown in FIGS. 1–3, and, optionally, one or more electrodes elsewhere in or on the surface of the patient's body. Preferably, control unit 90 conveys electrical energy to one or more of electrodes 100, in order to substantially stop motion of heart 20, and subsequently terminates application of the energy to enable the heart to beat again. Most preferably, control unit 90 is operated to intermittently stop or slow the activity of the heart, by repeated application and removal of the cardioplegia-inducing electrical energy. Use of the apparatus in this manner enables a surgeon to perform open-heart surgery or minimally-invasive surgery on the heart, generally without the use of chemical or hypothermic cardioplegia, and preferably without the need for cardiopulmonary bypass.

Preferably, the cardioplegia-inducing electrical energy comprises rapid pulses, generally similar in form and intensity to pulses used to pace the heart, which are applied through some of electrodes 100 coupled to heart 20. The pulses induce a reversible state of substantially constant contraction of most or substantially all of the heart muscle, without causing fibrillation or other dangerous arrhythmic activity. Typically, the cardioplegia induced during rapid pacing is sufficiently complete to allow the surgeon to perform surgery on (or adjacent to) the heart. Timing, shape, and magnitude parameters of the pacing pulses are described hereinbelow with reference to FIG. 5.

In some applications, control unit 90 applies a "fencing" signal, as described in the above-cited PCT and U.S. patent applications, to some of electrodes 100, in order to prevent generation of an action potential, and/or to prevent the propagation of an action potential from one region of the heart to another. Fencing is typically used to block or reduce the normal propagation of signals, generally yielding thereby a reduction of the force of contraction of the heart. Simultaneous application of fencing and rapid multi-site pacing, as provided by preferred embodiments of the present invention, has been found by the inventors to produce a substantially constant state of contraction, the contraction itself being of reduced force relative to normal contraction of the heart. Under these conditions, motion of the heart either stops essentially completely, or continues only as a very fine flutter. This condition is typically spontaneously reversible upon termination of application of signals to the heart. Thus, the heart typically resumes normal beating without assistance. Nevertheless, in order to even further increase the safety of some embodiments of the present invention, standard pacing, defibrillation and cardioversion means are additionally provided, in case normal beating is not spontaneously resumed.

Motion sensors 70, described hereinabove with reference to FIG. 1, are preferably coupled to or disposed in a vicinity of heart 20, and send signals to a motion analysis unit 80 of control unit 90. The signals provide feedback to the control unit, which adjusts some or all of the above-described electrical stimuli responsive to the motion sensor signals. Preferably, the motion sensors allow the control unit to calibrate the electrical stimuli which it delivers to the heart in order to minimize the heart's motion. Sensors 70 typically comprise one or more accelerometers. For example, one of the accelerometers may include a piezoelectric crystal, which produces an electric field responsive to deformation. Motion analysis unit 80 preferably comprises amplifiers to amplify low-level signals generated by motion sensors 70, and a signal processing unit, coupled to the amplifiers, which determines respective states of motion of the accelerometers. In some applications, motion analysis unit 80 additionally receives signals from one or more of supplemental sensors 72, particularly those sensors that detect mechanical phenomena such as blood flow rate and blood pressure.

Preferably, motion analysis unit 80 conveys results of its motion analysis to a "parameter search and tuning" block 84 of control unit 90, which iteratively modifies characteristics of the rapid multi-site pacing pulses and/or the fencing signal in order to reduce the measured heart motions. To achieve this goal, block 84 typically utilizes multivariate optimization and control methods known in the art (e.g., downhill simplex or linear state variable feedback or extended Kalman filter), in order to cause the measured motion and/or other parameters to converge to a desired value. For the purposes of some embodiments of the present invention, block 84 typically modifies a set of controllable parameters to minimize the aggregate motion of the heart.

Preferably, the controllable parameters are conveyed by block 84 to a signals generation block 86 of control unit 90, which generates, responsive to the parameters, electrical signals that are applied by electrodes 100 to the various sites on and in heart 20. Typically, but not necessarily, block 86 generates a combination of rapid multi-site pacing pulses and a fencing signal, as described herein. Preferably, block 86 comprises amplifiers and isolation elements known in the art of electrical signal conduction into a patient. Further preferably, block 86 is enabled to generate defibrillation and cardioversion signals in appropriate circumstances.

During the time periods when cardioplegia-inducing electrical energy is not being applied, the heart is supposed to be pumping blood essentially regularly. To verify proper cardiac function during these periods, an arrhythmia detection unit 82 of control unit 90 preferably receives inputs from sensors 70 and 72 and from electrodes 74 and 100, performs calculations responsive to the inputs, and conveys a signal to block 84 responsive to the calculations. Preferably, unit 82 employs techniques known in the art for determining an onset of arrhythmia, so that control unit 90 can treat or terminate the arrhythmia by applying, for example, regular pacing pulses or defibrillation pulses.

Additionally, during the time periods when cardioplegia-inducing electrical energy is being applied, the heart typically exhibits a fine fluttering motion. If arrhythraia detection unit 82 detects a substantial deviation from an expected motion profile or electrical activity profile, then it typically terminates application of the energy and initiates an anti-arrhythmic procedure under the surgeon's control.

Figure 5:
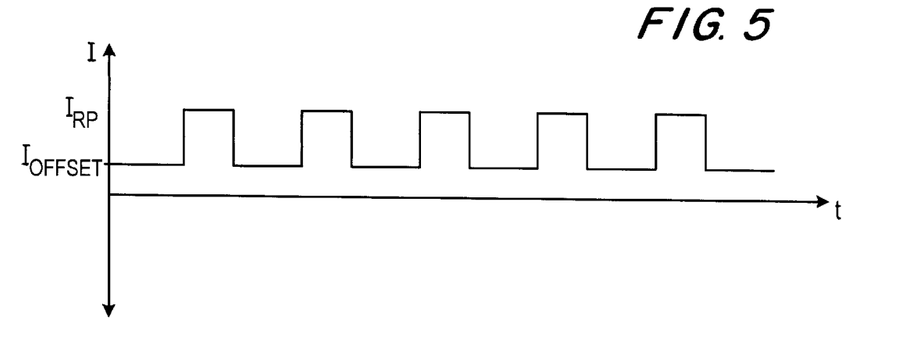
FIGS. 5 and 6 are graphs schematically illustrating electrical signals generated by the control unit of FIG. 4, in accordance with a preferred embodiment of the present invention.

FIG. 5 is a graph (not to scale) schematically illustrating pacing pulses generated by control unit 90, and applied to heart 20 by one or more of electrodes 100, in accordance with a preferred embodiment of the present invention. In a preferred rapid-pacing mode, control unit 90 generates a regularly-spaced series of square current pulses, injecting current through the one or more electrodes into underlying cardiac tissue, in order to generate a substantially constant contraction of the heart muscle. In this mode, the pulses are preferably characterized by a frequency above 5 Hz, and are typically applied above 10 Hz. Pulses applied between about 25 and 30 Hz have generally been shown to produce desirable results. In an experiment on a rabbit heart, a stimulation frequency above 100 Hz was found to be satisfactory. Other parameters typically characterizing the pulses include a duty cycle between about 5 and 50%, a DC offset ($I_{OFFSET}$) between about −10 and +10 mA, and an amplitude ($I_{RP}-I_{OFFSET}$) between about −20 and +20 mA. An amplitude of between about 1 and 5 mA is typically sufficient. These values are cited by way of example, and it will be understood that higher or lower frequencies and amplitudes may also be used, depending on the type and placement of the electrodes and on the specific condition of the patient's heart.

Typically, although not necessarily, each one of electrodes 100 conveys a particular waveform to heart 20, differing in certain aspects from the waveforms applied to the other electrodes. The particular waveform to be applied is determined by control unit 90, preferably under the control or supervision of the operator. Apects of the waveforms which are set by the control unit, and may differ from electrode to electrode, typically include parameters such as time shifts between application of waveforms at different electrodes, waveform shapes, amplitudes, DC offsets, durations, frequencies, duty cycles, shapes of rising and falling edges of pulses, gradual changes in amplitude or other parameters over multiple pulses, etc.

For example, although FIG. 5 shows the rapid pacing pulses as a series of monophasic square wave pulses, it will be understood by one skilled in the art that other waveforms, such as a sinusoid, a series of biphasic square waves, or substantially any shape known in the art of electrical stimulation of tissue, could be used in applications of the present invention. In some operational modes, the voltage applied by some or all of electrodes 100 is controlled, rather than the current, as described hereinabove and shown in FIG. 5. Generally, the shape, magnitude, and timing of the rapid pacing pulses are optimized for each patient, using optimization algorithms known in the art, in order to attain a desired level of stabilization of the heart. The optimizing process is preferably performed interactively at the beginning of a surgical procedure, and may be repeated automatically, at predetermined intervals, during the use of the cardioplegia-inducing apparatus. An interface, preferably comprising standard input means such as a foot-pedal and/or a keyboard, is typically provided to enable the surgeon to control the generated signals at any point prior to and during the surgical procedure.

For some applications, it is preferable to have a preconditioning period of the heart, during which the heart is exposed to initially short, and progressively longer periods of cardioplegia, as provided by some preferred embodiments of the present invention. For example, during the calibration period, the control unit may apply cardioplegia-inducing signals to create intermittent 2 second cardioplegia periods, followed by 4 second, 6 second, and longer periods, until a desired cardioplegia duration of 20 seconds is attained.

Preferably, application of the electrical stimuli in accordance with the present invention stabilizes the heart within a very short period, typically about 1 second, and can maintain the stability of the heart for prolonged periods, for example, 100 seconds, in order to allow the surgeon to perform surgery on a substantially non-moving heart. The heart typically returns to normal function within about 2 seconds of removal of the electrical stimuli. The method of preferred embodiments of the present invention thus does not harm the heart tissue and is spontaneously reversible, generally without requiring cardioversion or defibrillation as is sometimes needed following chemically-induced and thermally-induced cardioplegia.

Figure 6:
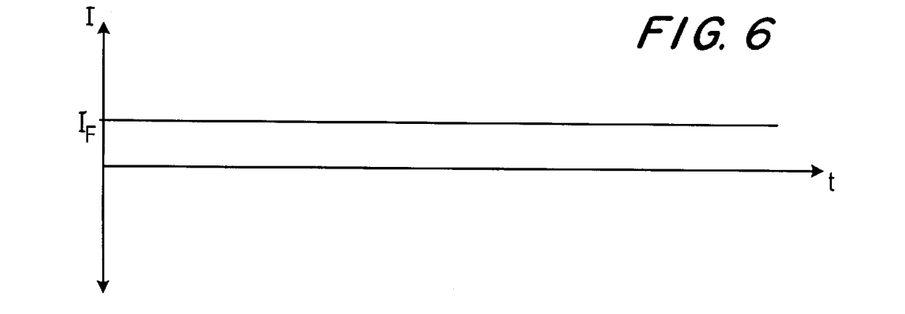

FIG. 6 is a graph schematically illustrating a fencing signal applied by a subset of electrodes 100 to respective sites on heart 20, in accordance with a preferred embodiment of the present invention. Preferably, as described hereinabove with reference to FIG. 4, the fencing signal is applied at the same time as the application of rapid pacing pulses by a second subset of electrodes 100, in order to reduce the force of contraction of the heart muscle. Typically, the magnitude of the fencing signal is between about −10 mA and +10 mA, although for some applications of the present invention, other values are appropriate. Additionally, although FIG. 6 shows the fencing signal as being DC, in some operational modes, the magnitude of the fencing signal may vary. Further additionally, the surgeon is preferably enabled to turn any of the signals described herein on and off during the signal-application period, in order to vary aspects of the contraction of the heart.

In some applications, standard pacing signals, delivered by one or more of electrodes 100 and/or by a previously-implanted pacemaker, are continued throughout most or all of a surgical procedure in which signals as provided by the present invention are applied. In these applications, application of the pacing signals is believed to help the heart maintain order in regions thereof which are not directly affected by the cardioplegia-inducing signals. It is additionally believed that continued application of the pacing signals may help improve an aspect of the heart's recovery from the cardioplegic period, e.g., to decrease the time before normal beating resumes. Furthermore, it is likely that many patients who undergo treatment using the apparatus and methods of the present invention will require pacing in any case.

Figure 7:
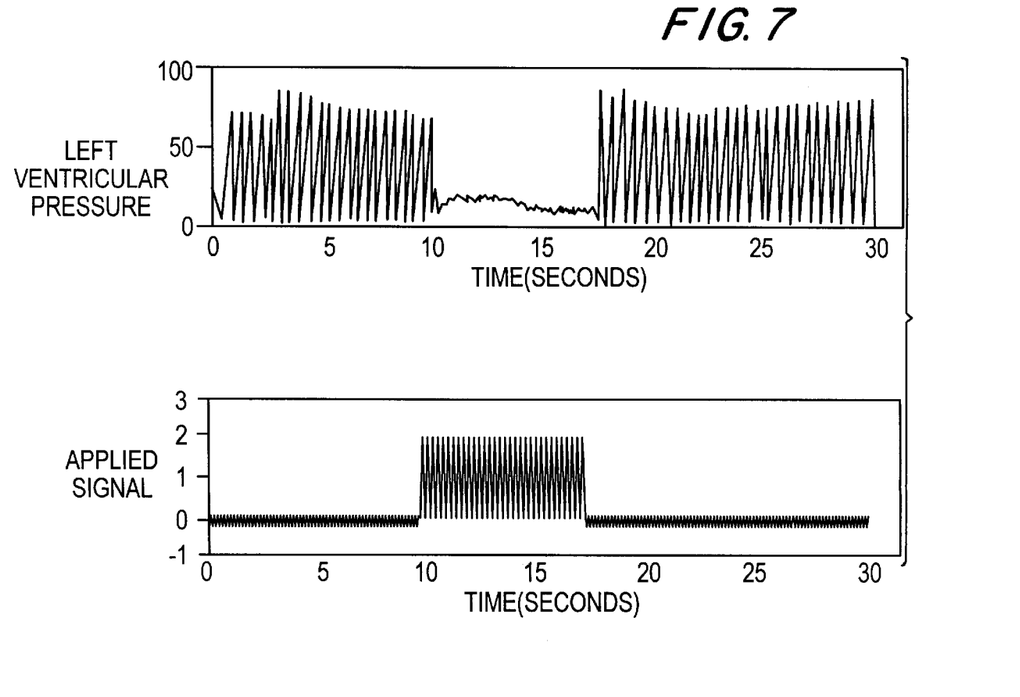
FIG. 7 schematically illustrates electrical signals applied to a dog's heart, in accordance with a preferred embodiment of the present invention, and experimental results obtained thereby.

FIG. 7 schematically illustrates electrical signals applied to an in vivo dog's heart, in accordance with a preferred embodiment of the present invention, and experimental results obtained thereby. During a control period (shown in the figure as lasting approximately 8 seconds, although in actuality the period could have been longer), the LVP is seen to be generally stable. Thereafter, the application of rapid pulses as provided by preferred embodiments of the present invention is associated with a marked drop in the LVP within 2 seconds from the initiation of the rapid pulses. Termination of rapid pulse application approximately 8 seconds from the initiation thereof is associated with a resumption of normal LVP within 2 seconds. FIG. 7 thus demonstrates the ability to control a global heart parameter using signals as provided by preferred embodiments of the present invention. A surgeon applying these signals is enabled to repeatedly induce and terminate the cardioplegic state within very short respective time periods, typically about 2 seconds. It is noted that no cardioplegia-inducing method known in the art has this capability.

Although preferred embodiments are described hereinabove with reference to electrical induction of cardioplegia to enable surgery on the heart, it will be understood that the present invention may be used for other purposes, in particular to enhance a physician's ability to perform diagnostic tests (e.g., magnetic resonance imaging) on the heart. Furthermore, the principles of the present invention are applicable not only to the heart, but also to controlling activity of other types of tissue, such as the intestines and other smooth, as well as skeletal, muscle.

It will be appreciated that the individual preferred embodiments described above are cited by way of example, and that specific applications of the present invention will typically employ features described with reference to a plurality of the Figures. The full scope of the invention is limited only by the claims.

What is claimed is:

1. A method for controlling activity of a heart of a living person during a medical procedure, comprising applying pulses to the heart at a rate greater than 5 Hz, so as to induce a spontaneously-reversible cardioplegia of the heart.

2. A method according to claim 1, wherein applying the signals comprises applying pulses at a rate greater than 10 Hz.

3. A method for controlling activity of a heart of a living person during a medical procedure, comprising:
   intermittently applying pulses to the heart so as to substantially stop motion of the heart and induce a spontaneously-reversible cardioplegia thereof;
   intermittently removing the pulses, to enable the heart to pump blood;
   sensing electrical activity of the heart to detect arrhythmia thereof; and
   during a time in which the cardioplegia-inducing pulses are removed, applying antiarrhythmic electrical energy to the heart to treat the arrhythmia.

4. A method for controlling activity of a heart of a living person during a medical procedure, comprising:
   applying electrical signals to the heart so as to induce a spontaneously-reversible cardioplegia thereof; and
   performing a diagnostic procedure on the person while the heart is in the cardioplegic state.

5. A method for controlling activity of a heart of a living person during a medical procedure, comprising:
   applying electrical signals to the heart so as to induce a spontaneously-reversible cardioplegia thereof; and sensing motion of the heart,
wherein applying the signals comprises modifying a characteristic of at least some of the signals applied to the heart responsive to the sensed motion.

6. A method according to claim 5, wherein sensing the motion comprises coupling at least one motion sensor to detect motion of a portion of the heart, wherein modifying the characteristic comprises modifying a signal characteristic so as to reduce the motion of the portion of the heart.

7. A method for controlling activity of a heart of a living person during a medical procedure, comprising:
applying electrical signals to the heart so as to induce a spontaneously-reversible cardioplegia thereof; and
applying a fencing signal to the heart to inhibit propagation of an activation wave therein while applying the electrical signals.

8. A method for controlling activity of a heart of a living person during a medical procedure, comprising applying to first and second sites of the heart respective first and second electrical waveforms, so as to induce a spontaneously-reversible cardioplegia of the heart, the second waveform differing from the first waveform.

9. A method for controlling activity of a heart of a living person during a medical procedure, comprising:
applying a first electrical signal, so as to preconditon a response of the heart to a second electrical signal; and
applying the second electrical signal to the heart, so as to induce a spontaneously-reversible cardioplegia thereof.

10. A method for controlling activity of a heart a living person during a medical procedure, comprising:
applying electrical signals to the heart so as to induce a spontaneously-reversible cardioplegia thereof, such that activity of the heart is reduced to a target level within 3 seconds of initiating such induction;
maintaining the cardioplegia for at least 10 seconds; and
terminating the cardioplegia, such that the heart resumes substantially normal function within 3 seconds.

11. A method for controlling activity of a heart of a living person during a medical procedure, comprising:
inducing cardioplegia of the heart, such that activity of the heart is reduced to a target level within 3 seconds of initiating such induction;
maintaining the cardioplegia for at least 10 seconds; and
terminating the cardioplegia, such that the heart resumes substantiallly normal function within 3 seconds.

12. Apparatus for controlling activity of a heart of a living person during a medical procedure, comprising:
one or more electrodes, adapted to be coupled to the heart; and
a control unit, adapted to actuate the electrodes to apply electrical signals to the heart at a rate greater than 5 Hz, so as to induce a spontaneously-reversible cardiplegia of the heart.

13. Apparatus according to claim 2, wherein the rate is greater than 10 Hz.

14. Apparatus for controlling activity of a heart of a living person during a medical procedure, comprising:
one or more electrodes, adapted to be coupled to the heart; and
a control unit, which is adapted to actuate the electrodes to apply electrical signals to the heart so as to induce a spontaneously-reversible cardioplegia thereof,
wherein the electrodes comprise one of more local sense electrodes, adapted to be coupled to the heart and to the control unit, which are adapted to sense electrical activity of the heart to detect arrhythmia thereof, and convey a signal responsive to the sensing to the control unit.

15. Apparatus for controlling activity of a heart of a living person during a medical procedure, comprising:
one or more electrodes, adapted to be coupled to the heart;
a control unit, which is adapted to actuate the electrodes to apply electrical signals to the heart so as to induce a spontaneously-reversible cardioplegia thereof; and
one or more motion sensors, adapted to be coupled to the heart and to the control unit, which are adapted to sense motion of the heart,
wherein the control unit is adapted to adjust the signals applied to the heart responsive to the motion.

16. Apparatus according to claim 15, wherein the control unit adjusts the signals so as to minimize the sensed motion.

17. Apparatus for controlling activity of a heart of a living person during a medical procedure, comprising:
one or more electrodes, adapted to be coupled to the heart; and
a control unit, which is adapted to actuate the electrodes to apply electrical signals to the heart so as to induce a spontaneously-reversible cardioplegia thereof,
wherein the signals include a first signal, which preconditions a response of the heart to a subsequent signal, which induces the cardioplegia.

18. Apparatus for controlling activity of a heart of a living person during a medical procedure, comprising:
one or more electrodes, adapted to be coupled to the heart;
a control unit, which is adapted to actuate the electrodes to apply electrical signals to the heart so as to induce a spontaneously-reversible cardioplegia thereof,
wherein the signals induce cardioplegia of the heart, such that activity of the heart is minimized within 3 seconds of initiating such induction, such that the cardioplegia is maintained for at least 10 seconds, and such that upon termination of the cardioplegia, the heart resumes substantially normal function within 3 seconds.

19. Apparatus for controlling activity of a heart of a living person during a medical procedure, comprising a control unit adapted to generate, for application to the heart, an electrical signal which induces cardioplegia of the heart, such that activity of the heart is minimized within 3 seconds of initiating such induction, such that the cardioplegia is maintained for at least 10 seconds, and such that upon termination of the generation of the electrical signal, the heart resumes substantially normal function within 3 seconds.

20. A method for performing a medical procedure on smooth muscle, comprising:
applying electrical signals to the smooth muscle so as to reduce activity thereof, such that the activity increases spontaneously upon removal of the signals; and
performing the procedure while the activity is reduced.

21. A method for performing a medical procedure on skeletal muscle, comprising:
applying electrical signals to the skeletal muscle so as to reduce activity thereof, such that the activity increases spontaneously upon removal of the signals; and
performing the procedure while the activity is reduced.

22. A method for performing a diagnostic procedure on a muscle, comprising:
applying electrical signals to the muscle so as to reduce activity thereof, such that the activity increases spontaneously upon removal of the signals; and
performing the diagnostic procedure while the activity is reduced.

* * * * *